United States Patent [19]

Bark et al.

[11] Patent Number: 4,659,021

[45] Date of Patent: Apr. 21, 1987

[54] PROCESS FOR PRODUCING PURIFIED BROMINATED AROMATIC COMPOUNDS

[75] Inventors: Wendell G. Bark, Baton Rouge, La.; John C. Parks, Ballwin, Mo.

[73] Assignee: Ethyl Corporation, Richmond, Va.

[21] Appl. No.: 791,309

[22] Filed: Oct. 25, 1985

Related U.S. Application Data

[63] Continuation of Ser. No. 558,495, Dec. 6, 1983, abandoned.

[51] Int. Cl.[4] .................. B02C 19/12; C07C 41/22
[52] U.S. Cl. .............................. 241/18; 241/23; 568/639; 570/211
[58] Field of Search ............... 568/639; 570/211; 241/23, 30, 24, 17, 18, 57, 65, 21

[56] References Cited

U.S. PATENT DOCUMENTS

Re. 30,778 10/1981 Hahn et al. ............... 241/18
2,240,718  5/1941 Schiffman et al. ......... 241/23 X
4,327,227  4/1982 Ayres et al. .............. 568/639

FOREIGN PATENT DOCUMENTS 2027762 12/1971 Fed. Rep. of Germany ........ 241/23

Primary Examiner—Mark Rosenbaum
Attorney, Agent, or Firm—Donald L. Johnson; John F. Sieberth; J. D. Odenweller

[57] ABSTRACT

A process for purifying crude brominated aromatic compounds such as decabromodiphenyl oxide containing impurities. The crude brominated aromatic compound undergoes a single processing step of grinding in the presence of heated air. The temperature is sufficient to effect substantial removal of impurities and yet remains below the melting point of the brominated aromatic compound.

15 Claims, No Drawings

PROCESS FOR PRODUCING PURIFIED BROMINATED AROMATIC COMPOUNDS

BACKGROUND OF THE INVENTION

This application is a continuation of application Ser. No. 558,495 filed Dec. 6, 1983, now abandoned.

1. Field of the Invention

This invention relates to the purification of brominated aromatic compounds. More particularly, this invention relates to a process for purifying brominated aromatic compounds containing impurities such as residual free bromine and by-product hydrogen bromide. Crude decabromobiphenyl oxide readily lends itself to this purification procedure since it is a solid, thermally stable compound.

2. Description of the Prior Art

Traditional purification techniques are not successful with all brominated aromatic compounds. Recrystallization in particular is often difficult. Decabromobiphenyl oxide has limited solubility in available solvents thus making recrystallization both cumbersome and uneconomical.

U.S. Pat. No. 4,327,227 describes a process for producing purified brominated aromatic compounds. The purification process involves sequentially grinding and then heating the crude solid brominated aromatic compounds. However, this process involves two distinct steps and is not the most efficient and economically desirable means of accomplishing the purification. Considerable handling and hence increased investment would be required if separate drying and grinding process steps were employed.

It has been discovered that by simultaneously drying and grinding a crude solid brominated aromatic compound that a superior brominated aromatic compound can be obtained.

Accordingly, it is a primary object of this invention to teach a process for producing purified brominated aromatic compounds that is superior to the techniques that heretofore have been employed. A two-fold advantage is obtained. The process is more economically attractive and a superior purified product results.

SUMMARY OF THE INVENTION

The present invention claims a process for purifying crude brominated aromatic compounds such as decabromodiphenyl oxide containing impurities comprising a single processing step of grinding the crude brominated aromatic compound in the presence of heated air at a temperature sufficient to effect substantial removal of the impurities.

DESCRIPTION OF THE PREFERRED EMBODIMENTS

The subject of this invention is a process for purifying a crude solid brominated aromatic compound containing impurities comprising a single processing step of drying and grinding the brominated aromatic compound in the presence of heated air at a temperature sufficient to remove water or volatiles and to effect substantial removal of the impurities. Typical brominated aromatic compounds that may be purified using the process of the present invention include any brominated aromatic compound that is typically a solid. Mixtures of brominated aromatic compounds may also be purified following the single processing step of the present invention. The brominated aromatic compounds must withstand the high temperatures reached during the simultaneous drying and grinding step. An important parameter in selecting brominated aromatic compounds is therefore the thermal stability of the material. By thermally stable it is meant that the crude brominated aromatic compound can be heated to a temperature of about 140° C. to about 300° C. without melting and significant discoloration.

A popular use for thermally stable brominated aromatic compounds is in the flame-retardant area. High levels of purity are required for brominated aromatic compounds useful as flame retardants in polymer compositions. These brominated products should have extremely low levels of residual impurities such as free bromine, hydrogen bromide, by-product bromine containing derivatives, retained catalysts and the like. The presence of such impurities can have undesirable effects on the polymer compositions. Purity is particularly important from the standpoint of color. Thermal stability under the processing conditions in commercial molding operations is also an essential parameter.

Typical brominated aromatic flame retardants that may be purified following the process of the present invention includes decabromobiphenyl oxide, octabromobiphenyl oxide, pentabromoethylbenzene, ethylene-bis-tetrabromophthalimide and the like. The only qualification necessary is that the aromatic brominated compound must be a solid and have sufficient thermal stability to withstand heat treatment at a temperature of about 140° C. to about 310° C. The preferred brominated aromatic compound intended for use in the practice of the present invention is decabromobiphenyl oxide.

The crude brominated aromatic compound undergoes a single processing step of grinding in the presence of heated air. This simultaneous dry and grind may be conducted in several ways. The process may be performed in any suitable grinding equipment that is modified or designed so as to allow heated air to come in contact with the solid particles. Typical grinding equipment includes an air mill, sand mill, ball mill, hammer mill, impact mill, air-swept mill and the like. Air milling procedures are preferred for large scale grinding of crude brominated aromatic compounds.

The type of impurities present in the brominated aromatic compounds vary depending on the brominated aromatic compound selected. The most common impurities typically present include, occluded free bromine, hydrogen bromide, brominated by-products and the like. By simultaneously drying and grinding the crude solid reaction mass substantial removal of these impurities is accomplished. Exact identification of the impurities is not required in the practice of the present invention. A substantial decrease in the amount and types of impurities results.

At least one manufacturer makes equipment designed to simultaneously dry and grind wet solid particles. This is the Pulvocron by Bepex Corporation. The registered trademark Pulvocron refers to a series of fine grinding systems. The Pulvocron pulverizer is an airswept, combination pulverizer/classifier with external fineness adjustment during operation. Solid particles can be pulverized in the medium-fine, fine and ultrafine particle size ranges down to less than 5 microns top size.

The Pulvocron employs one or more beater plates, around the periphery of which are attached rigid hammers of hard metal. It is driven within a casing at clearances of small fractions of an inch, the periphery of which is generally corrugated with V-notches or square notches. Feed enters around the driving shaft and is first broken by breaker plates on the first disk. It then travels circumferentially with an axial component to a classifying chamber, in which is a separately driven and controlled rotor with vanes. The volume of air carries the fine particles inward to an axial discharge opening, while the coarse particles are kept outward by centrifugal force. They discharge into a tailings return line, along with some of the air, and return to a low-pressure area near the axis of the inlet.

It is important to note that any set-up which involves a single processing step of drying and grinding is effective in the practice of the present invention.

The temperature of the air during the grinding process is sufficient to effect the removal of water or volatiles as well as substantial removal of impurities. The minimum temperature that permits the benefits of this invention to be achieved is about 100° C. The temperature is generally above 150° C. since this temperature allows for substantial removal most of the free halogen from the crude product. The maximum temperature employed in the practice of the present invention is about 310° C. The maximum temperature that is employed cannot exceed the melting point of the brominated aromatic compound. For instance, the melting point of decabromobiphenyl oxide is about 310° C. therefore the heated air used during the grinding step cannot exceed this temperature. The temperature during the dry and grind process is given as a range because the temperature of the air entering the system is not identical to the temperature of the exit air. The system cools down a number of degrees during the process as the hot air vaporizes some of the impurities present in the crude brominated aromatic product. The preferred temperature range is from about 150° C. to about 310° C. More preferably, the temperature is from about 180° C. to about 310° C. The most preferred temperature range depends on the brominated aromatic compound being purified. Ideally, the temperature is as high as possible yet it does not exceed the melting point of the brominated aromatic compound selected. It is speculated that high temperatures allow for maximum diffusion of free occluded bromine out of the brominated aromatic compound particles.

There is no preferred time frame in which to conduct the process of the present invention. Rather, the time for the single dry and grind process depends on the equipment selected and the final particle size range desired. Generally, the single processing step of drying and grinding is conducted for a few seconds to about one hour. If a Pulvocron system is used then the process of the present invention only requires a few seconds to three minutes.

The purified brominated aromatic particles that result from the practice of the present invention are preferably less than about 20 microns in diameter and substantially entirely less than about 100 microns in diameter. The term "predominantly" is used herein to mean that a substantial proportion of the particles (i.e., about 50% or more by weight) are less than the specified diameter (e.g., 20 microns) but that appreciable amounts (e.g., up to about 50% by weight) of larger particles may be present consistent with the objectives of this invention. More preferably, the brominated aromatic compound particles are substantially entirely less than about 15 microns in diameter with at least about 90% of the particles being less than about 5 microns in diameter and the particles being predominantly less than about 3 microns in diameter.

The following examples demonstrate the purification of decabromobiphenyl oxide using a single processing step of drying and grinding. The following examples are not intended to limit the subject invention in any way.

EXAMPLE 1

A sample of crude decabromobiphenyl oxide was prepared by mixing biphenyl oxide with some $AlCl_3$ catalyst in a mixing tank. The contents of the mixing tank was then added to a reactor which contained bromine and the remaining catalyst. The reaction continued for about ten hours. It was an exothermic reaction so once the temperature reached 50° C. the reaction was cooled to maintain approximately 50° C. during the remainder of the reaction.

The reaction mixture was transferred to a strip pot containing water. The temperature ultimately reached 100° C. as the excess bromine was stripped off. The mixture was then cooled and caustic was added to achieve a pH of 12. The decabromobiphenyl oxide/water slurry was then transferred to a slurry tank for product recovery. It is this decabromobiphenyl oxide which was purified in the manner shown by the examples below.

EXAMPLE 2

A comparison was made between a variety of purification methods used on the crude decabromobiphenyl oxide of Example 1. The crude decabromobiphenyl oxide had an average particle size range of about 50 microns to 120 microns.

The purification methods involved a variety of procedures. The heading "Type of Treatment" in Table 1 contains a listing of each purification procedure that was conducted. A brief description of temperature and processing time is given when warranted. A comparison was made between each of these treatment procedures by contrasting the free halogen present in the initial crude decabromobiphenyl oxide sample with the free halogen content of the final product. The mean particle size range after purification is also listed. Note that not all of the purification procedures involved grinding therefore the mean particle size after purification was quite large.

Types of treatment included grinding, an NaOH heating and wetting with 5% NaOH then dried, washed and redried. Examples in Table 1 involve use of the Bepex machine which dried and ground the crude decabromobiphenyl oxide in one processing step.

Grinding was conducted using a hammer mill unless otherwise indicated. An alternate grinding procedure involved the use of a mortar and pestle.

The NaOH cook was conducted by adding a volume of 25% NaOH in water plus additional water to a glass-lined or glass vessel. The solid crude decabromobiphenyl oxide was added to the vessel and heated. After the cook, the solids were dried and optionally ground to the desired particle size.

The exit temperature for the single dry and grind processing step refers to the temperature of the heated air as it leaves the system. For the purposes of Table 1, the duration of treatment was approximately one minute.

TABLE 1

| Type of Treatment | Conditions | Free Halogen Initial | Free Halogen Final | Mean Particle Size |
|---|---|---|---|---|
| Ground only | | 192 | 150 | 9 |
| Ground/NaOH cook | 70° C.-2 hours | 192 | 55 | 9 |
| Heat in oven | 230° C.-overnight | 192 | 120 | 116 |
| Ground(mortar/pestle)/NaOH cooked | 70° C.-2 hours | 260 | 140 | 68 |
| Heat in oven | 230° C.-overnight | 240 | 40 | 74 |
| Ground/Heat in oven | 230° C.-overnight | 260 | 56 | 11 |
| NaOH cooked | 70° C.-2 hours | 260 | 220 | 86 |
| Ground/NaOH cooked | 70° C.-2 hours | 260 | 140 | 9 |
| NaOH cooked | 70° C.-21 hours | 260 | 240 | 52 |
| Wetted with 5% NaOH dried/washed/dried | | 260 | 244 | 96 |
| Single step dry & grind | 220° C. exit temp. | 160 | 32 | 2.7 |
| Single step dry & grind | 220° C. exit temp. | 60 | 16 | 3.0 |
| Single step dry & grind | 220° C. exit temp. | 300 | 80 | 2.6 |
| Single step dry & grind | 220° C. exit temp. | 160 | 32 | 2.9 |
| Single step dry & grind | 220° C. exit temp. | 256 | 20 | 2.7 |
| Single step dry & grind | 220° C. exit temp. | 12 | 24 | 2.5 |
| Single step dry & grind | 220° C. exit temp. | 168 | 12 | 3.0 |
| Single step dry & grind | 220° C. exit temp. | 232 | 24 | 2.8 |

As indicated by Table 1, the most dramatic decrease in free halogen content of the purified decabromobiphenyl oxide was observed in the crude decabromobiphenyl oxide that was treated using the singly drying and grinding process step. The time required for this dramatic improvement was also minimal compared to the processing time listed earlier in Table 1.

We claim:

1. A process for purifying a crude wet unground solid brominated aromatic compound containing impurities including elemental bromine and hydrogen bromide, said process comprising mixing said crude wet unground brominated aromatic compound with a current of pre-heated air and grinding said crude brominated aromatic compound while in said current of pre-heated air for a time period of a few seconds up to 3 minutes whereby said pre-heated air raises the temperature of said crude brominated aromatic compound to a temperature sufficient to effect substantial removal of said impurities but below the melting point of said brominated aromatic compound.

2. A process of claim 1 wherein said crude solid brominated compound is crude solid decabromobiphenyl oxide.

3. A process of claim 2 wherein said grinding provides particles of decabromobiphenyl oxide predominantly less than about 20 microns in diameter and substantially entirely less than about 100 microns in diameter.

4. A process of claim 3 wherein said particles of decabromobiphenyl oxide are substantially entirely less than about 15 microns in diameter with at least about 90% of the particles being less than about 5 microns in diameter and the particles being predominantly less than about 3 microns in diameter.

5. A process of claim 3 wherein said impurities are occluded free bromine, hydrogen bromide and brominated by-product.

6. A process of claim 5 wherein said single processing step is conducted for a few seconds.

7. A process of claim 1 wherein said temperature is above 150° C. and below the melting point of said brominated aromatic compound.

8. A process of claim 7 wherein said brominated aromatic compound is decabromobiphenyl oxide.

9. A process of claim 8 wherein said temperature is in the range of 180°-310° C.

10. A process of claim 9 wherein said grinding is carried out in an air mill.

11. A process of claim 10 wherein said time period does not exceed 1 minute.

12. A process of claim 9 wherein said grinding is carried out in an impact mill.

13. A process of claim 12 wherein said time period does not exceed 1 minute.

14. A process of claim 1 wherein said time period does not exceed 1 minute.

15. A process of claim 14 wherein said time period is a few seconds.

* * * * *

UNITED STATES PATENT AND TRADEMARK OFFICE
CERTIFICATE OF CORRECTION

PATENT NO. : 4,659,021

DATED : APRIL 21, 1987

INVENTOR(S) : WENDELL G. BARK ET AL.

It is certified that error appears in the above-identified patent and that said Letters Patent is hereby corrected as shown below:

Column 6, lines 25-26 reads "single processing step" and should read -- grinding -- .

Delete Claim 10 and insert -- 10. A process of Claim 9 wherein said time period does not exceed 1 minute. -- .

Delete Claim 11 and insert -- 11. A process of Claim 10 wherein said time period is a few seconds. -- .

Delete Claim 12 and insert -- 12. A process of Claim 9 wherein said grinding is carried out in an air mill. -- .

Delete Claim 14 and insert -- 14. A process of Claim 9 wherein said grinding is carried out in an impact mill. -- .

Delete Claim 15 and insert -- 15. A process of Claim 14 wherein said time period does not exceed 1 minute. -- .

Signed and Sealed this

Eighteenth Day of August, 1987

*Attest:*

DONALD J. QUIGG

*Attesting Officer*  *Commissioner of Patents and Trademarks*